United States Patent [19]

Baba et al.

[11] Patent Number: 4,888,703
[45] Date of Patent: Dec. 19, 1989

[54] APPARATUS FOR MONITORING THE TOXICANT CONTAMINATION OF WATER BY USING AQUATIC ANIMALS

[75] Inventors: Kenji Baba; Hayao Yahagi; Shoji Watanabe; Naoki Hara, all of Hitachi; Mikio Yoda, Tokai; Shunji Mori, Hitachi; Takashi Iida, Hitachi; Takashi Katori, Hitachi; Masahiko Ishida, Hitachi, all of Japan

[73] Assignees: Hitachi Engineering Co., Ltd.; Hitachi, Ltd., both of Tokyo, Japan

[21] Appl. No.: 93,034

[22] Filed: Sep. 4, 1987

[30] Foreign Application Priority Data

| Sep. 9, 1986 | [JP] | Japan | 61-210798 |
| Sep. 9, 1986 | [JP] | Japan | 61-210800 |
| Nov. 25, 1986 | [JP] | Japan | 61-278830 |
| Dec. 5, 1986 | [JP] | Japan | 61-288849 |
| Jan. 16, 1987 | [JP] | Japan | 62-6000 |
| Jan. 21, 1987 | [JP] | Japan | 62-9878 |

[51] Int. Cl.$^4$ ............................................. G01N 00/00
[52] U.S. Cl. ............................................ 364/496; 119/3; 364/150; 364/420; 364/517
[58] Field of Search ............... 364/496, 150, 420, 517; 119/3; 362/3, 5; 354/291

[56] References Cited

U.S. PATENT DOCUMENTS

| 656,769 | 8/1900 | Hunter | 354/291 |
| 1,053,887 | 2/1913 | Sontag | 354/291 |
| 1,575,478 | 3/1926 | Earle | 354/291 |
| 3,039,357 | 6/1962 | Eagle | 354/291 |
| 4,626,992 | 12/1986 | Greaves et al. | 364/150 |
| 4,723,511 | 2/1988 | Solman et al. | 119/3 |
| 4,740,805 | 4/1988 | Germond | 354/291 |

FOREIGN PATENT DOCUMENTS 0938864  6/1982  U.S.S.R. .................................. 119/3

Primary Examiner—Bruce Y. Arnold
Assistant Examiner—Terry S. Callaghan
Attorney, Agent, or Firm—Antonelli, Terry & Wands

[57] ABSTRACT

A fish is bred in a transparent basin, into which water to be tested is supplied. A light source and a television camera are arranged in such a manner that images of the fish are taken by the camera as a silhouette. From the thus obtained fish images, the frequency distribution of the gravity centers of the fish images in the direction of the depth of water are obtained. The abnormality of the behavior of the fish is detected by comparison of the obtained frequency distribution with a reference distribution provided in advance.

13 Claims, 14 Drawing Sheets

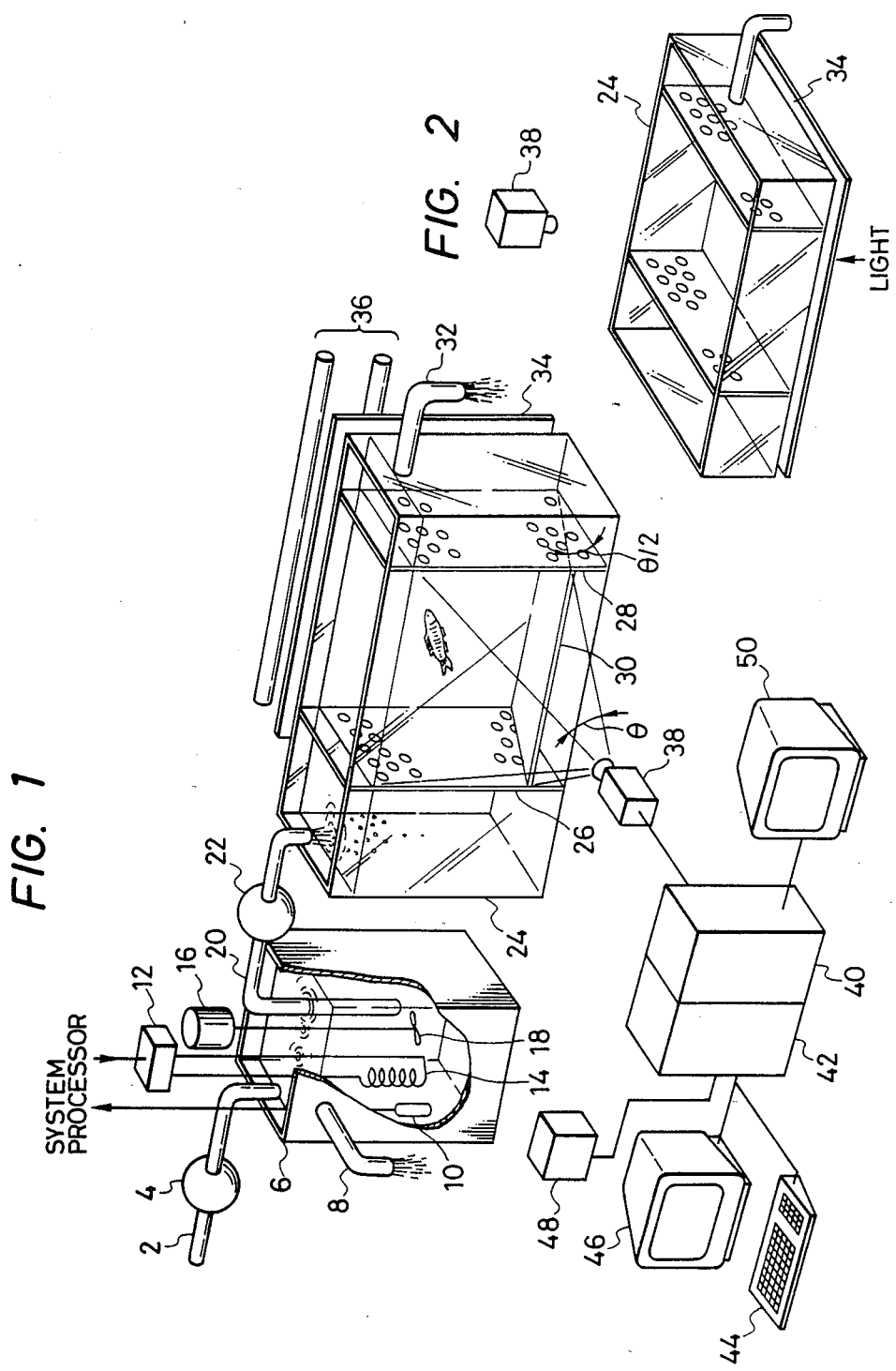

(GRAY IMAGE)

(BINARY IMAGE)

GRAY IMAGE
($t = t_0$)

GRAY IMAGE
($t = t_0 + \Delta t$)

(IMAGE BY TERNARY DATA)

($t = t_0$)

($t = t_0 + \Delta t$)

B−A

B
(t=t₀+Δt)
A
(t=t₀)
BINARY IMAGE

BINARY IMAGE
(EXCLUSIVE - ORed)

FIG. 19a
(BINARY IMAGE)
FIG. 19b
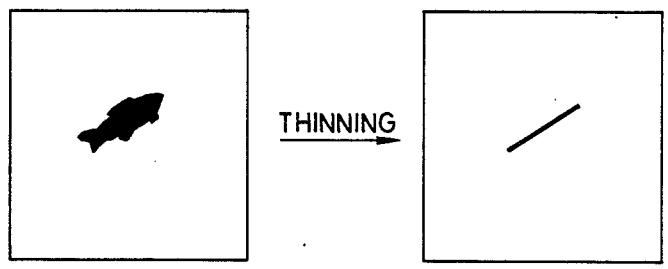
THINNING
FIG. 20
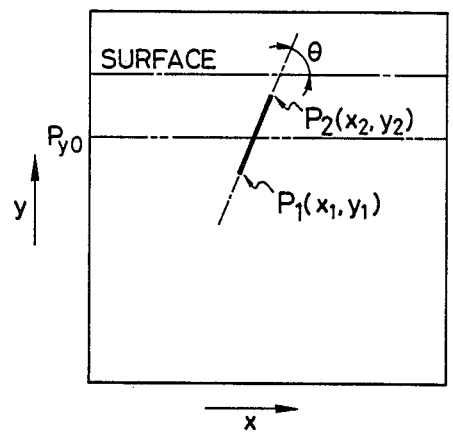
FIG. 21
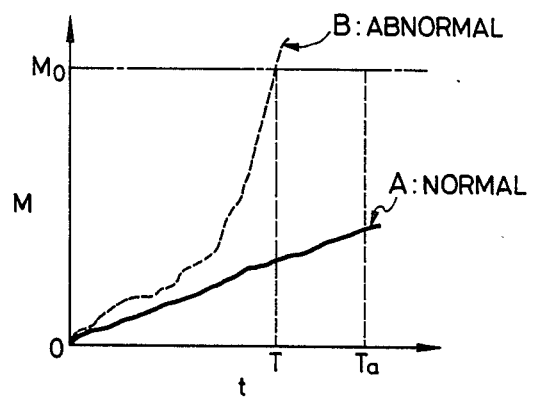

APPARATUS FOR MONITORING THE TOXICANT CONTAMINATION OF WATER BY USING AQUATIC ANIMALS

BACKGROUND OF THE INVENTION

1. Field of The Invention

The present invention relates to an apparatus for monitoring the toxicant contamination of water by using aquatic animals, more particularly to an apparatus for detecting the contamination of water with toxic material by monitoring the behavior of the aquatic animals bred in the water to be tested by means of the image processing technique.

2. Description of The Related Art

In a water purification plant, it must be always monitored whether or not toxic material, especially acute toxicity, is mixed in raw water. If the toxicant contamination of raw water is detected, the intake of raw water into the plant has to be stopped immediately. As a matter of course, it is necessary to monitor that toxic material is not mixed in the purified water which is processed in the plant. Also in a sewage treatment plant, it must be monitored whether or not toxic material is mixed in the water which is processed in the plant, before the processed water is discharged therefrom.

In this manner, it is necessary in every water processing plant to always monitor whether or not toxic material is mixed in the water flowing into the plant and/or flowing out therefrom. To this end, aquatic animals such as carp, crucian carp, dace, bitterling, rainbow trout and so on have been bred in a basin supplied with a part of water to be tested, and a person has to watch, by the visual observation, the abnormal behavior of such aquatic animals occurring when acute toxicity is mixed in the water. Therefore, it has been difficult to continuously watch the behavior of the aquatic animals and to detect early the toxicant contamination of the water to be tested.

To improve this, there has been proposed an apparatus as disclosed in the article "System for sensing toxicant in raw water" in pages 464 to 466 of the proceedings of The 36th Annual Conference of Japan Waterworks Associaton held in Miyazaki, Japan, in May, 1985. According to the method disclosed therein, a fish selected from among those as mentioned above is bred in a basin, which is supplied with a part of water to be tested. In the article, the water to be tested is considered as being contaminated with acute toxicity, when the fish drifts on the surface of the water often or for long time, turning its venter upward.

The basin is lighted from above and the behavior of the fish is observed by a television camera installed above the basin, i.e., on the same side as a light source. In an image taken by the camera, the fish drifting in such a manner as mentioned above is recognized as a bright spot which is independent and larger than a predetermined size. The toxicant contamination of water is judged on the basis of the existence of the bright spot in the image and/or the time-dependent change in the occurrence rate thereof.

However, the prior art as mentioned above has some problems. When light is projected to a fish drifting on the surface of water from above, there is the difference in the brightness of the light reflected from the fish in accordance with parts thereof. For example, the light reflected by the ventral part of the fish is brightest and that reflected by the dorsal part thereof is darkest. The brightness of light reflected by various fins of the fish lies between those of lights reflected by the ventral and dorsal parts thereof.

In order that a fish is clearly recognized, distinguished from a background, there must be a considerable difference in the brightness between the fish and the background. Namely, the brightness of the background is necessary to be selected at the value much brighter than that of the ventral part the fish or at the value much darker than that of the dorsal part thereof. However, the color of the dorsal and ventral parts of a fish changes through a year and the intensity of light reflected therefrom also changes accordingly. Therefore, it is difficult and troublesome to determine and change the level of the brightness of the background in accordance with the seasonal change in the color of a body of a fish.

Further, the brightness of the reflected light also changes in accordance with the postural angle of a fish with respect to the light projected thereon and therefore the ventral part of the fish often shines in silver when the fish turns. The inventors have found through their experiment that, from such various factors as mentioned above, it is very difficult to recognize a fish at high accuracy through a year by means of the image recognition technique according to the prior art, even though the brightness of the background is selected to be deep black or pure white. If water to be tested becomes turbid, the accuracy of recognition is further deteriorated.

SUMMARY OF THE INVENTION

An object of the present invention is to provide an apparatus for monitoring the toxicant contamination of water by using aquatic animals, by which the behavior of the aquatic animals can be clearly observed by means of an image recognition technique without any influence of various factors which deteriorate the accuracy of recognition thereof.

A feature of the present invention is that, in an apparatus for monitoring the toxicant contamination of water which comprises a basin for breeding an aquatic animal, into which a part of water to be tested is introduced, a light source for lighting up the basin, a television camera for taking an image of a predetermined area of the basin and a processor for processing the image taken by the camera to observe the behavior of the aquatic animal and to produce an alarm signal when the abnormal behavior of the aquatic animal is observed, the television camera is provided on the side opposite to the light source with respect to the basin.

According to this feature, since an image of an aquatic animal is taken as a silhouette, the recognition of the aquatic animal is not influenced by any factors, such as the seasonal change in the color of the body of the aquatic animal, the postural change during the movement of the aquatic animal, and so on.

Further detailed objects and features of the present invention will be understood from reading the following description and inspection of the drawings.

BRIEF DESCRIPTION OF THE DRAWINGS

FIG. 1 schematically shows an apparatus for monitoring the toxicant contamination of water according to an embodiment of the present invention;

FIG. 2 shows another example of the relation of a television camera, a breeding basin and a light source in the apparatus of FIG. 1;

FIGS. 19a and 19b, FIG. 20 and FIG. 21 are drawings for explaining the operation of the flow chart of FIG. 18.

DESCRIPTION OF THE PREFERRED EMBODIMENTS

Figure 3:
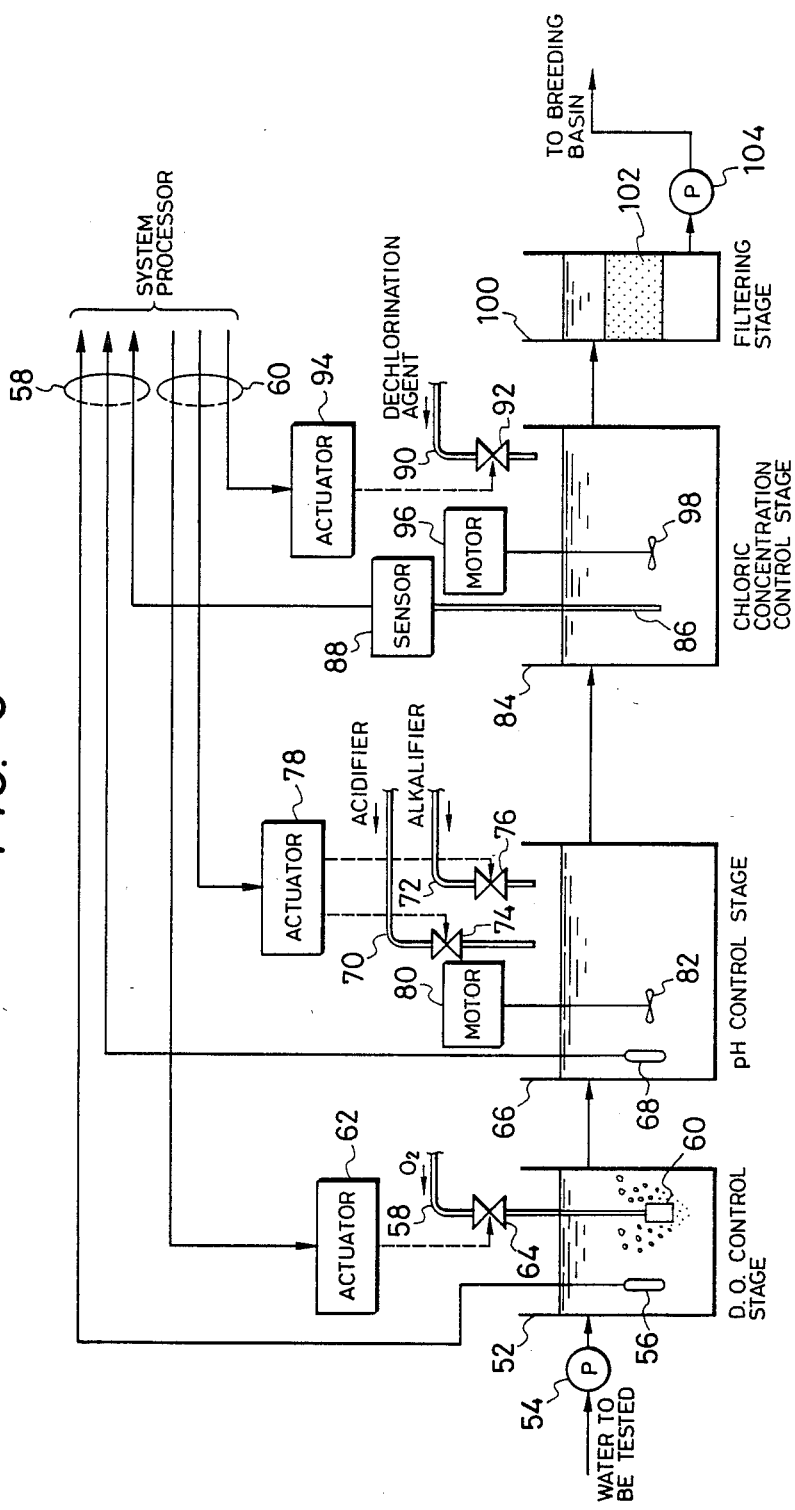
FIG. 3 shows some examples of devices for adjusting the breeding environment of aquatic animals.

In the following, the description will be made of an apparatus for monitoring the contamination of water with acute toxicity according to an embodiment of the present invention, referring to the accompanying drawings. The present invention can be applied to various kinds of water processing plants, in which it is necessary to monitor the toxicant contamination of water, such as a water purification plant and a sewage treatment plant. For the simplification of the description, however, the following explanation will be made of a water purification plant.

In FIG. 1, a conduit 2 introduces a part of water to be tested into a water temperature adjusting device by a pump 4. In the plant of this embodiment, the water to be tested is raw water taken from a river or other resources. The behavior of an aquatic animal greatly depends on various factors of the environment surrounding it. The water temperature is one of the most important environmental factors. The water temperature adjusting device keeps the water temperature constant so that the behavior of the aquatic animal can be observed under the steady condition. Further, the control of other environmental factors will be described later, referring to FIG. 3.

The water temperature adjusting device comprises a tank 6, in which a predetermined amount of the introduced raw water is stored. Excess water flows out from a discharge pipe 8. The temperature of the water within the tank 6 is detected by a temperature sensor 10, and an output of the sensor 10 is led to a system processor which is referred to later. The system processor receives the signal from the sensor 10 and produces a temperature control signal, which is given to a heater actuator 12. The actuator 12 supplies the electric current for a heater 14 provided within the water in accordance with the temperature control signal, so that the water temperature is maintained at a desirable value set in accordance with the kind of a bred fish, for example about 15° to 20° C. for carp, crucian carp and bitterling and about 10° to 20° C. for rainbow trout. Although only the heater 14 is provided in FIG. 1, there can be added a cooling device, if necessary. Further, a motor 16 rotates an agitator 18 to make the temperature of the water within the tank 6 uniform.

The water whose temperature is adjusted is supplied by a pump 22 to a breeding basin 24 through a conduit 20. The basin 24 is made of material such as transparent glass or acrylate resin. Within the basin 24, a room is defined by perforated plates 26, 28 and a plate 30. In the room is bred an aquatic animal, which is selected from among carp, crucian carp, dace, bitterling, rainbow trout and other kinds of fish which live in a river from which raw water is taken. Excess water flows out from a discharge pipe 32.

Behind the basin 24 there is provided a translucent plate 34, which scatters light of a light source 36 to uniformly light up the basin 24 from behind. The translucent plate 34 is made of ground glass or paper. In front of the basin 24, i.e., on the opposite side of the light source 36 with respect to the basin 24, there is provided a television camera 38. As apparent from the arrangement as mentioned above, the camera 38 can take an image of a fish as a silhouette. Therefore, the image of the fish can be taken as a contrast image and therefore without any influence caused by the seasonal change of the color of the body of the fish.

Compared with the prior art, in which a fish is recognized by a light reflected therefrom, the intensity of light of the light source 36 is sufficient to be very low. According to the inventors' experiment, a fish could be clearly recognized with the light of 230 to 270 luxes, whereas the light of 2500 luxes were estimated to be necessary in the prior art. As a result, the stress imposed on a fish is very large in the prior art. The continuous, strong stress causes the abnormal behavior of the fish and it results in the misleading of the monitoring of the toxicant contamination of water. Such a low intensity of light as in the present invention prevents such a misleading.

Further, it will be understood that the room defined by the plates 26, 28 and 30 is for the purpose of limiting the movement of the fish within the field of view of the camera 38. Therefore, the plate 30 must be inclined at the angle $\theta/2$ with respect to the bottom of the basin 24, assuming that the angle of the field of the camera 38 is $\theta$.

Another example of the positional relation of the basin 24, the camera 38 and the light source is shown in FIG. 2. The basin 24 in this example is rather flat. Therefore the light source is provided under the basin 24 and the behavior of a fish is observed by the camera 38 installed over the basin 24. Also with this arrangement, the image of the fish can be taken as a silhouette. In FIG. 2, the camera 38 and the light source can be inversely located with respect to the basin 24. Further, it is possible to combine the arrangement shown in FIG. 1 with that shown in FIG. 2. With the combined arrangement, the behavior of a fish can be observed in two dimensions. Accordingly it is useful when plural fish are bred in the basin 24, because two fish are distinguishably recognized even if they position overlapping each other when viewed from one direction.

Returning to FIG. 1, image signal produced by the camera 38 is led to an image processor 40, which carries out the predetermined processing on the image signal sent from the camera 38. The image processing conducted by the image processor 40 will be described in detail later. A monitor display 50 is connected to the image processor 40 in order to monitor the photographing condition by the camera 38 and the necessary observation result.

The image processor 40 is further coupled to a system processor 42 by means of a system bus (not shown). The system processor 42 executes various processing on the basis of data given from the image processor 40 and produces an alarm signal when the toxicant contamination of water to be tested is detected. The processing operation carried out by the system processor 42 for monitoring the toxicant contamination of water will be explained together with the processing operation of the image processor 40 later.

Further, the system processor 42 also carries out the control of the water temperature on the basis of the signal from the temperature sensor 10. Since this water temperature control is performed by a usual feed-back control, the further description of the processing operation for this control in the processor 42 is omitted. In addition to or in replacement of the water temperature control as mentioned above, other environmental factors may be controlled by the system processor 42, if necessary. The control of those environmental factors will be explained later, referring to FIG. 3.

In order to input various constants and variables necessary for the operation of the system processor 42, a key board 44 and a character display 46 are coupled thereto. They are inputted from the key board 44, while being monitored by the character display 46. In the same manner, the constants and variables necessary for the operation of the image processor 40 are given by the key board 44 through the system processor 42. The alarm signal produced by the system processor 42 is led to an alarm device 48 to inform persons of the toxicant contamination of the water.

Referring next to FIG. 3, the explanation will be made of the control of the various environmental factors.

In the figure, a first stage of the control of the environmental factors is the dissolved oxygen control, by which the concentration of oxygen dissolved in water to be tested is adjusted. A dissolved oxygen control device comprises a tank 52, into which water to be tested is introduced by a pump 54. An oxygen sensor 56 is provided to detect the concentration of the dissolved oxygen in the water. An output signal of the sensor 56 is led to the system processor 42, which receives the signal and produces a control signal accordingly. Air sent through a pipe 58 is supplied to the water by a diffuser 60. The amount of air supplied to the water is adjusted by a control valve 64, which is controlled by an actuator 62 in accordance with the control signal from the system processor 42.

With this control stage, the concentration of the dissolved oxygen in the water to be tested can be kept at the desired value. The target value is set closely to the saturated oxygen concentration, desirably more than 5 mg/lit.. Further, since this control is also performed by a usual feed-back control, the further description of the processing operation for this control in the processor 42 is omitted.

The water whose concentration of the dissolved oxygen has been adjusted is introduce into a pH control stage. Although a pump is provided in order to introduce the water from the prior control stage into this stage, it is omitted in the figure. A pH control device in this stage comprises a tank 66, in which a pH sensor 68 is provided. An output signal of the sensor 68 is led to the system processor 42, which produces a control signal in accordance with the signal from the sensor 68. In order to adjust the value of pH of the water, acidifier or alkalifier is added to the water through pipes 70 and 72 from respective reservoirs (not shown). The amount of those agents is adjusted by a control valve 74 or 76, which is controlled by an actuator 78 in accordance with the pH control signal from the system processor 42. A motor 80 rotates an agitator 82 to make the value of pH of the water uniform.

The value of pH of the water is desirable to be maintained about 6 to 8, i.e. substantially neutral. Further, since this pH control can be achieved by a usual feed-back control, the further explanation of the processing operation for this control in the processor 42 is omitted.

Next, the water is introduced into the chloric concentration control stage, by which the dechlorination of the water is carried out. Also in this case, a pump, which introduces the water from the prior stage to this stage, is omitted in the figure. A part of the water within a tank 84 is given to a chlorine concentration sensor 88 through a pipe 86. The sensor 88 detects the concentration of chlorine and produces an output signal. The output signal of the sensor 88 is led to the system processor 42, which produces a control signal accordingly. A dechlorination agent, such as sodium thiosulfate, is sent from a reservoir thereof (not shown) through a pipe 90 and added to the water. The amount of the agent to be added is adjusted by a control valve 92, which is controlled by an actuator 94 in accordance with the control signal from the system processor 42. A motor 96 rotates an agitator 98 to make the concentration of chlorine in the water uniform.

Although chlorine is added for disinfection of water, the concentration thereof.is desirable to be as low as possible for the purpose of the present invention, because the high concentration thereof greatly affects a fish bred in the water. Therefore, this stage is desirable to control the concentration of chlorine so as to be almost zero. Also in this stage, the control can be performed by a usual feed-back control and therefore the further description of the processing operation for this control in the processor 42 is omitted.

Further, with the same construction as the chloric concentration control stage as described above, the concentration of ammonia in water to be tested can be controlled. In that case, an ammonia concentration sensor and a deammoniation agent must be used in place of the chlorine concentration sensor 88 and the dechlorination agent in the chlorine concentration control stage. Similarly to the case of the chlorine concentration, the ammonia concentration is to be controlled as low as possible, desirably at almost zero.

If water to be tested is so turbid that the accurate recognition of the image of a fish is influenced thereby, it can be introduced into a filtering stage. Although a pump is provided in order to introduce the water from the prior stage to the filtering stage, it is omitted in the figure. A filtering device in this stage comprises a tank 100 and a filter element 102 equipped therein. The filtered water is led by a pump 104 to the breeding basin 24 directly or through the water temperature adjusting device as shown in FIG. 1. With this filtering, it becomes possible to recognize the image of a fish clearly.

In an example of the environmental factor control described above, the control stages for several kinds of the environmental factors were coupled in cascade, including the water temperature control stage shown in FIG. 1. All of them are not necessary to be always provided, but some of them can be selected in accordance with the nature of water to be tested and other necessities of control. The order of the selected control stages is also determined arbitrarily. Further, in the example of FIG. 3, every control stage has an individual tank 6, 52, 66 or 84. It is also possible to provide necessary control equipment and sensors corresponding thereto in a single tank. However, the filtering stage is to be provided independently therefrom.

Moreover, in an example shown in FIGS. 1 and 3, the outputs of the sensors 10, 56, 68 and 88 are led to the system processor 42, in which the control signals necessary for the control of the respective environmental factors are obtained. Since, however, these controls are performed by means of a simple, usual feed-back control, they can be carried out by individual control devices separately provided for the respective factor controls.

Figure 4:
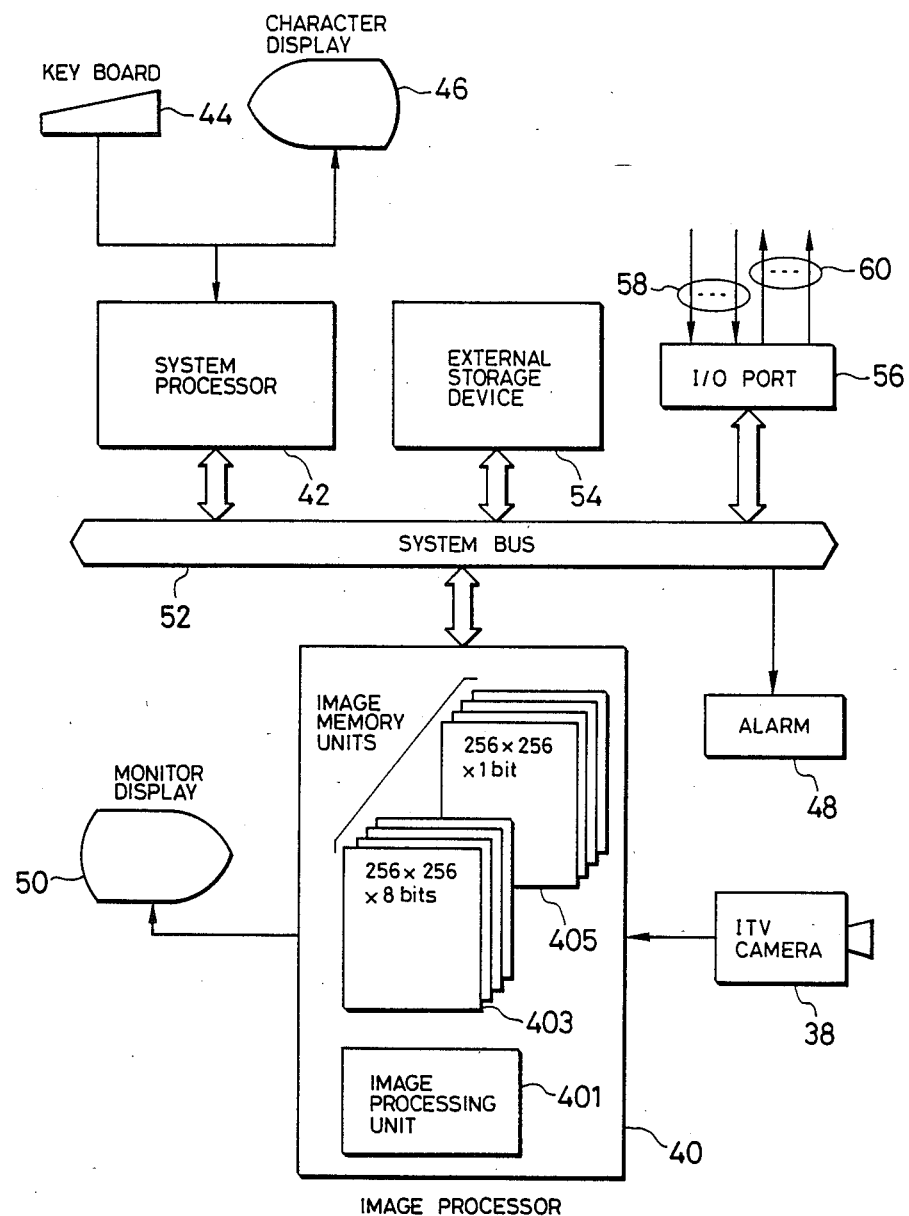
FIG. 4 is a block diagram schematically showing the configuration of a data processing system for monitoring the toxicant contamination of water to be tested.

Referring next to FIG. 4, the description will be made of a processing system, which is mainly composed of the image processor 40 and the system processor 42 coupled with each other by a system bus 52. In the figure, the same reference numerals represent the identical parts to those in FIG. 1.

In the configuration of FIG. 4, an external storage device 54 is connected to the system bus. The storage device 54 stores data processed by the system processor 42 for record and/or other purposes. To the system bus 52 is also coupled an input/output port 56, through which the signals are given to the system processor 42 from the sensors 10, 56, 68 and 88 and the control signals obtained by the processing operation in the system processor 42 are sent out to the actuators 12, 62, 78 and 94. To this end, a group of lines 58 for inputting the sensor signals and a group of lines 60 for outputting the control signals are connected to the I/O port 56. The detailed function and operation of the processing system mentioned above will be made apparent in the following description.

The image processor 40 comprises an image processing unit 401 having the histogram processing function, the labeling function, the feature extracting function, the convolution processing function and so on as an ordinary image processing unit has, and image memory units 403 and 405, one (403) of which is a memory for gray image data produced by the camera 38 and the other (405) is a memory for binary image data processed by the image processing unit 401. Assuming that one frame of the image taken by the camera 38 is composed of 256×256 pixels, one unit of the gray image memory 403 has the storage capacity of 256×256×8 bits, and one unit of the binary image memory 405 has that of 256×256×1 bits. In the image processor 40 used in the inventors' experiment, both the gray image memory 403 and the binary image memory 405 are composed of four units, respectively.

Similarly to a usual processing apparatus of this kind, there are further provided other facilities such as an analog to digital converter for converting an analog image signal taken by the camera 38 into a digital signal, a digital to analog converter for converting the processed digital data into an analog signal for display in the monitor display 50 and various interfaces. In FIG. 4, however, they are omitted for simplification of the drawing.

Figure 5:
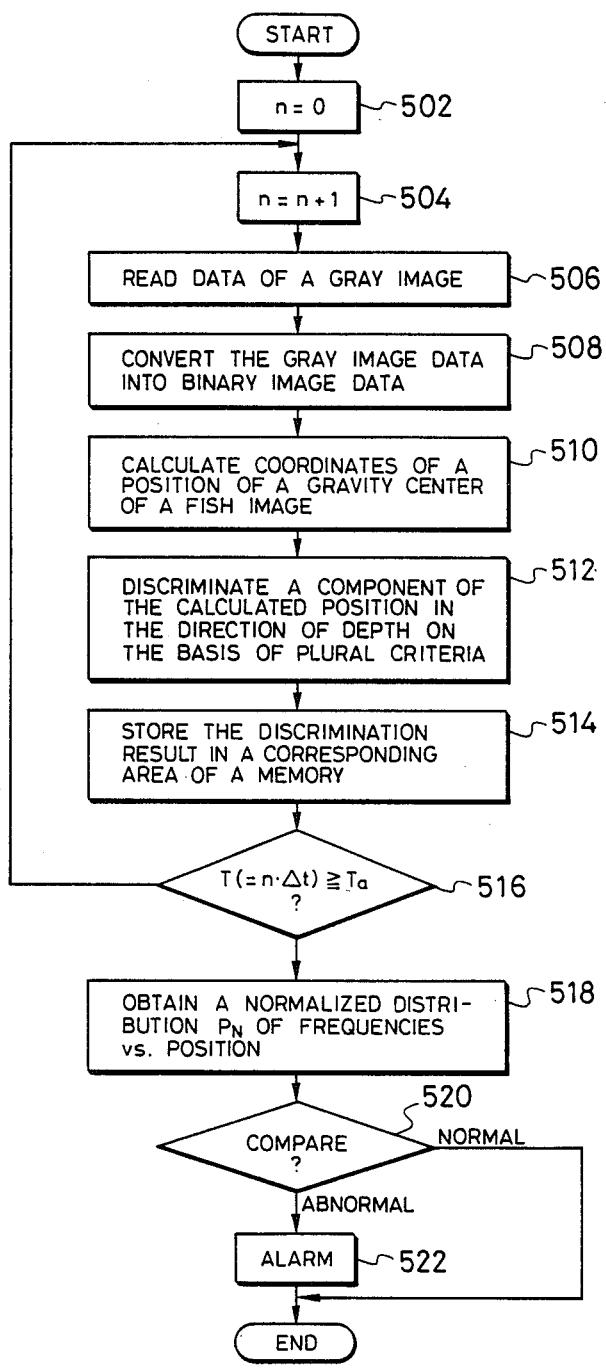
FIG. 5 is a flow chart showing one example of the operation of the data processing system of FIG. 4.

In the flow chart of FIG. 5, there is shown the processing operation of the processing system mentioned above. It is to be noted that this flow chart includes the processing operations of both the image processor 40 and the system processor 42. When the operation starts, first of all, n representative of the number of repetition times of the following loop operation is set at zero at step 502. After n is increased by one at step 504, data of a gray image is read from the gray image memory 403 at step 506. Then, at step 508, the gray image data read at step 506 is converted into binary image data. The converted binary image data is stored in the binary image memory 405.

Figure 6A:
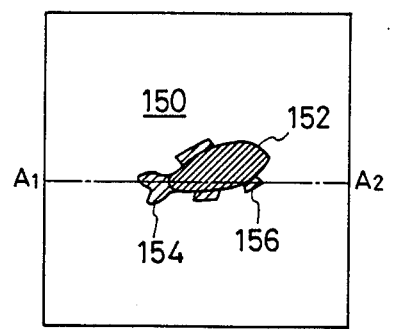
FIGS. 6a to 6d and FIGS. 7a and 7b are drawings for explaining the operation illustrated by the flow chart of FIG. 5.

The conversion from the gray image to the binary image is explained, referring to FIGS. 6a to 6d. Fig. 6a shows an example of a gray image taken by the camera 38 and stored in the gray image memory 403. As already described, an image of a fish is taken as a silhouette in the gray image. Namely, as shown in FIG. 6a, the gray image taken by the camera 38 is composed of a very bright part 150 of a background and an almost deep dark image 152 of the fish.

Figure 6B:
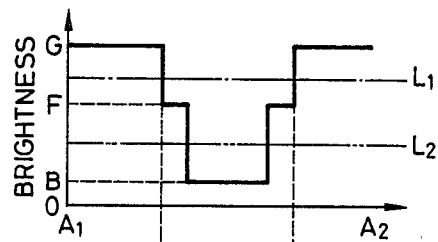

If the gray image as shown in FIG. 6a is scanned along the line $A_1$-$A_2$, there can be obtained the brightness distribution with respect to pixels on the line $A_1$-$A_2$ as shown in FIG. 6b. As shown in the figure, in the gray image, the background 150 assumes the highest brightness level G and a part of the body 152 of the fish assumes the lowest level B which is close to almost the black. The brightness of parts of various fins 154, 156 lies in the level F between the level G of the background and that B of the body 152.

Figure 6C:
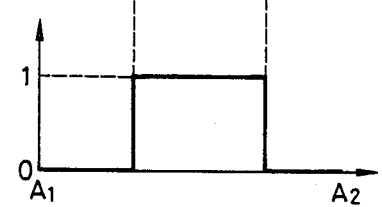

Let us express the brightness of a pixel (x, y) in the gray image of FIG. 6a by B(x, y), wherein x and y represent horizontal and vertical coordinate values, respectively, when taking X axis in the horizontal direction of the gray image of FIG. 6a and Y axis in the vertical direction thereof. The brightness B(x, y) of each pixel is compared with a threshold as shown by $L_l$. If the comparison output is made the binary "0" when B(x, y) is higher than $L_l$ and the binary "1" when B(x, y) is lower than $L_l$, the binary signal as shown in FIG. 6c can be obtained. Further, a threshold $L_2$ in FIG. 6b is used in another embodiment and therefore referred to later.

Figure 6D:
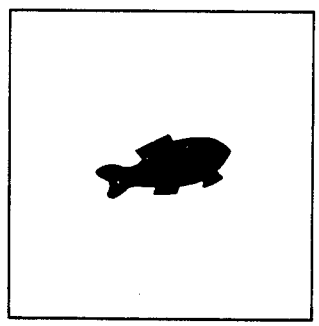

If the scanning and the comparison with the threshold $L_l$ are carried out over the whole of the gray image of FIG. 6a, the binary image signals as shown in FIG. 6c can be obtained with respect to all the scanning lines of the gray image and they are stored in the binary image memory 405. On the basis of the binary image data stored in the memory 405, the binary image as shown in FIG. 6d can be obtained. In this image, the binary signal "0" is expressed as white and "1" as black.

Returning to FIG. 5, at step 510, a position $G(x_g, y_g)$ of a gravity center of a fish image is calculated on the basis of the binary image data stored in the memory 405. Further, similarly to the case of the gray image of FIG. 6a, it is assumed that X axis of the coordinates is taken in the horizontal direction of the binary image as shown in FIG. 6d, and Y axis in the vertical direction thereof, i.e., in the direction of the depth of water. Moreover, as will be described later, n times of the calculation of the gravity center are repeated by the loop operation for one observation period. If, therefore, the coordinates of the gravity center is generally expressed by $G_n$ ($x_{gn}$, $y_{gn}$), they are calculated in accordance with the following formulas:

$$x_{gn} = \left( \sum_{j=1}^{J} x_{nj} \right)/J \quad (1)$$

$$y_{gn} = \left( \sum_{j=1}^{J} y_{nj} \right)/J \quad (2)$$

In the above formulas, J denotes the total number of pixels included in a fish image, i.e. having the binary "1" in the binary image, $x_{nj}$ the coordinate on the X axis of a j-th one of the above pixels, and $y_{nj}$ the coordinate on the Y axis of the j-th pixel.

Then, at step 512, a component ygn, i.e., a vertical component, of the thus calculated gravity center is compared with plural criteria $Y_{gn}(k)$ (k=1,2, ..., K) prepared for the discrimination and it is judged to what class of the criteria it belongs. For example, if $Y_{gn}(k) \leq ygn \leq Y_{gn}(k+1)$, the discrimination result is made k. On the other hand, there are provided in a memory of the system processor 42 plural storage areas each operating as a counter, the number of which is equal to that K of the criteria prepared for the aforesaid discrimination, and each of which corresponds to the respective discrimination result k. At step 514, the discrimination result is stored. Namely, when the vertical component $y_{gn}$ of the calculated gravity center meets the aforesaid relation, the content of the counter area corresponding to the discrimination result k is increased by one.

Next at step 516, the lapse of time T from the beginning of the observation is judged. For this judgment, the time period $T_a$ is set as one observation time period in advance. If T does not exceed $T_a$, the operation returns to step 504, and n is increased by 1. Thereafter, the aforesaid operation is repeated. Namely, the operation mentioned above is a loop operation, which is repeated until T reaches $T_a$.

The lapse of time T is expressed by the product of the number n of repetition times of the loop operation and the time period $\Delta t$ necessary for one loop operation. The time period $\Delta t$ depends on the processing speed of the processors 40 and 42, generally is about 0.1 to 2.0 seconds and the observation time $T_a$ will be set at a few minutes to one hour. In the processing system used in the inventors' experiment, t was about 0.5 seconds and $T_a$ was set at nine minutes.

Figure 7A:
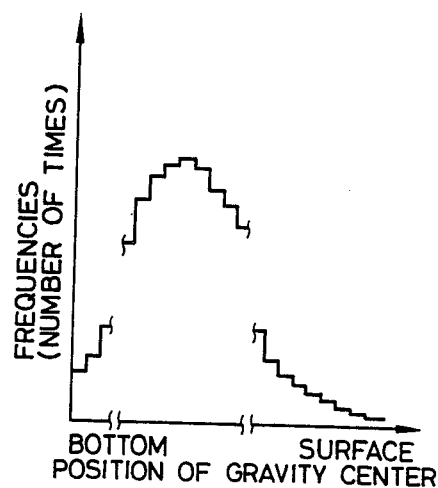

When one observation time $T_a$ has lapsed, there can be obtained in the plural counter areas of the memory of the system processor 42 the distribution of frequencies with respect to the vertical positions of the gravity centers. FIG. 7a shows an example of the thus obtained distribution. The total number of the gravity centers obtained during one observation time is determined by $T_a/\Delta t$, which is equal to the number N of repetition times of the loop operation. In the inventors' experiment, the total number of the gravity centers calculated during one observation time is 1,080, because $\Delta t$ and $T_a$ are 0.5 seconds and 9 minutes, respectively.

The thus obtained distribution of frequencies versus the vertical positions of the gravity centers is normalized at step 518, in accordance with the following formula:

$$Ti \ P_N(k) = P(k)/N \quad (3)$$

wherein k is an integer representing a class of the criteria prepared for the discrimination of the calculated gravity centers, P(k) the frequencies of occurrence of the gravity centers belonging to the criterion class k, and $P_N(k)$ a normalized value thereof.

Figure 7B:
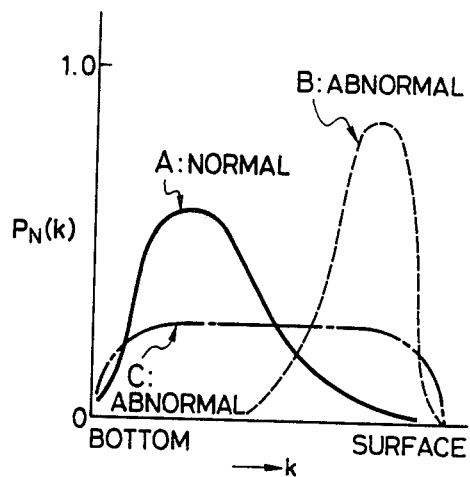

Examples of the thus obtained normalized distribution of frequencies versus the gravity centers are shown in FIG. 7b. It is discriminated on the basis of the thus obtained distributions whether or not the behavior of the fish is normal. This discriminating operation will be explained in detail, referring to FIG. 7b. In the figure, there are shown three kinds of the normalized distributions of frequencies versus the gravity centers. A solid line A represents the normalized distribution when the behavior of the fish is normal. As shown by the solid line A, when the fish is normal, it often positions in the portion close to the bottom rather than in the portion close to the surface of water.

When the fish moves abnormally in the neighborhood of the surface of water because of the toxicant contamination of water, the normalized distribution becomes as shown by a broken line B. When the fish moves abnormally upward and downward because of the toxicant contamination of water, the normalized distribution becomes as shown by a chain line C. Accordingly, it is possible to judge on the basis of the comparison of the profiles of the normalized distributions whether or not the behavior of the fish is normal. The comparison of the profiles of the distributions can be achieved by a known statistical method.

Returning again to FIG. 5, at step 520, the comparison as mentioned above is carried out. If the behavior of the fish is judged to be normal, the operation ends and waits the start of the next time of the observation. If, at step 520, the behavior of the fish is judged to be abnormal, the alarm signal is given to the alarm device 48 at step 522 and thereafter the operation ends.

Figure 8A:
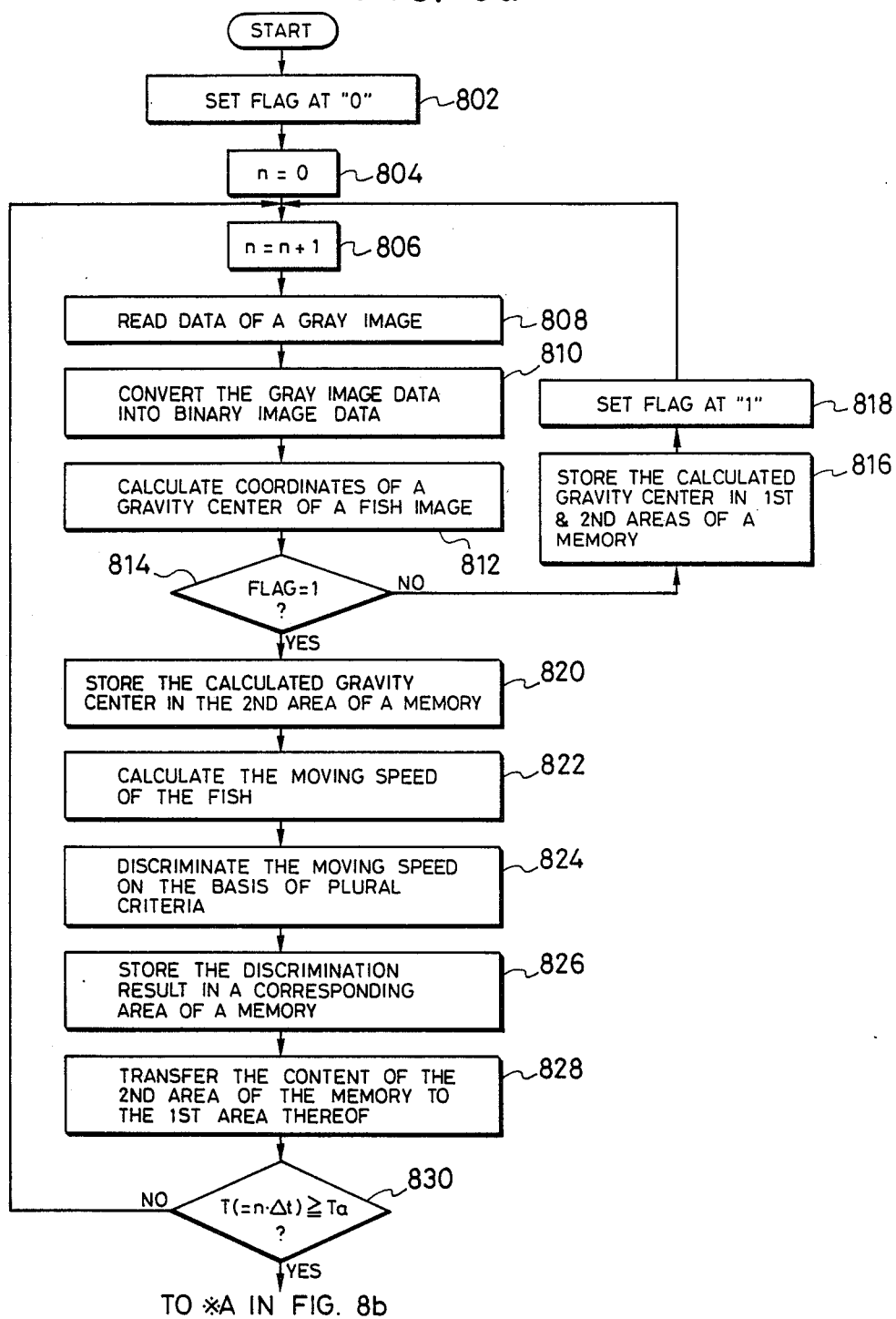
FIGS. 8a and 8b are a flow chart of another example of the operation of the data processing system of FIG. 4.
Figure 8B:
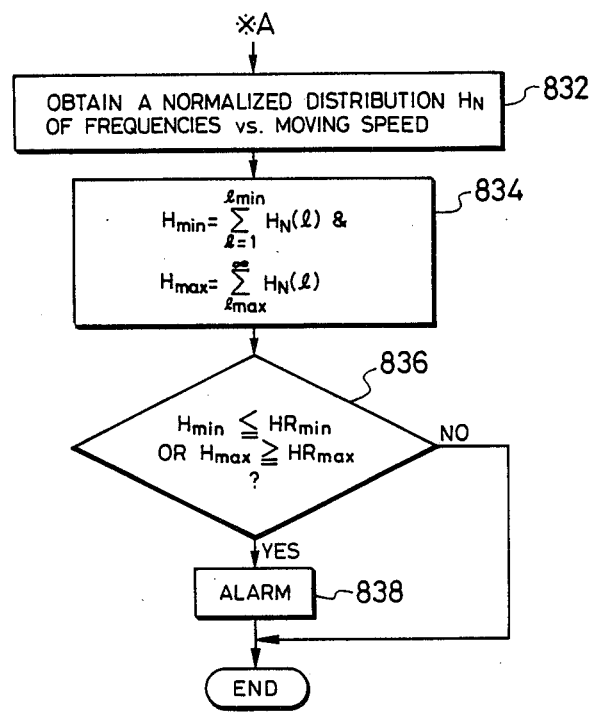

In the following, there will be described another embodiment, in which the abnormal behavior of a fish is detected by the moving speed of the fish. FIGS. 8a and 8b show a flow chart of the processing operation carried out for this embodiment in the processing system.

In FIG. 8a, after the operation starts, a flag is set at "0" at step 802. Thereafter, steps from 804 to 812 are the same as those 502 to 510, and the gravity center of the fish image is calculated. Then, in this embodiment, it is checked at step 814 whether or not the flag is "1". If the flag is not "1", the operation goes to step 816, at which the obtained gravity center is stored in both first and second storage areas provided in a memory of the system processor 42 for storing the calculated gravity centers. Then, after the flag is set at "1", the operation returns to step 86. At step 806, n is increased by 1, and the calculation of the gravity center is carried out on a fish image of the next gray image, again.

When the operation reaches step 814, the flag is checked. Since the flag must be "1" Z at this time, the operation is branched to step 820, at which the gravity center calculated for the second time is stored in the second storage area of the memory, i.e., the content of the second storage area is rewritten by a newly calculated gravity center. At step 822, the moving speed $V_l$ of the fish is calculated on the basis of the contents of the first and second storage areas of the memory in accordance with the following formula:

$$V_1 = \sqrt{(x_{g1} - x_{g2})^2 + (y_{g1} - y_{g2})^2} \times 1/\Delta t \quad (4)$$

wherein $x_{gl}$ and $y_{gl}$ represent the horizontal and vertical coordinates of the gravity center obtained for the first time, and $x_{g2}$ and $y_{g2}$ represent those obtained for the second time. Further, as described later, the calculation of the moving speed as mentioned above is repeated plural times. If, therefore, the above formula is generally rewritten for the n-th time, it becomes as follows:

$$V_n = \sqrt{(x_{gn} - x_{gn+1})^2 + (y_{gn} - y_{gn+1})^2} \times 1/\Delta t \quad (5)$$

At step 824, the thus obtained moving speed $V_n$ is compared with plural criteria $V_n(l)$ (l=1, 2, ..., L) prepared for the discrimination and it is judged to what class of the criteria it belongs, wherein l is an integer representing a class of the criteria. For example, if $V_n(l) \leq V_n < V_n(l+1)$, the discrimination result is made l. On the other hand, there are in a memory of the system processor 42 plural storage areas each operating as a counter, the number of which is equal to that L of the criteria prepared for the aforesaid discrimination, and each of which corresponds to the respective discrimination result l. On the basis of the discrimination result, the content of a corresponding one of the counter areas is increased by one at step 826. Then, at step 828, the content of the second area of the memory is transferred to the first area thereof. Thereafter, it is discriminated at step 830 whether or not the lapse of time T exceeds the time $T_a$ set for one observation time period in advance.

Figure 9A:
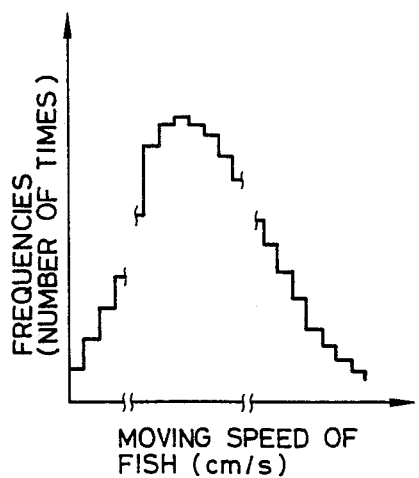
FIGS. 9a and 9b are drawings for explaining the operation illustrated by the flow chart of FIGS. 8a and 8b.

If T does not exceed $T_a$, the operation returns to step 806, and after n is increased by 1, the operation mentioned above is repeated again. This loop operation is repeated until T reaches $T_a$. Further, the minor loop composed of steps 816 and 818 is executed only once at the first time of the repeating operations in every observation. By the repetition of this loop operation, the distribution of frequencies versus the moving speeds of the fish as shown in FIG. 9a is obtained. In the operation mentioned above, the relation of n, $\Delta t$, T and $T_a$ is quite the same as that in the case of FIG. 5.

At step 832 in FIG. 8b, the thus obtained distribution of frequencies versus the moving speeds of the fish is normalized by the total number N of the moving speeds obtained for one observation period in accordance with the following formula:

$$H_N(l) = H(l)/N \quad (6)$$

In the formula (6), H(l) represents frequencies of occurrence of the moving speed belonging to the criterion class l, and $H_N(l)$ a normalized value thereof.

Figure 10:
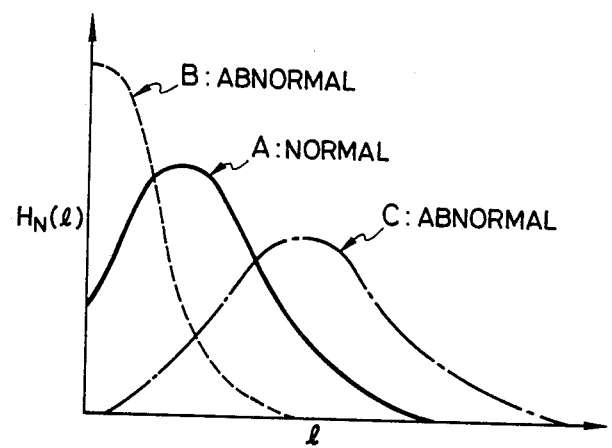
Figure 9B:
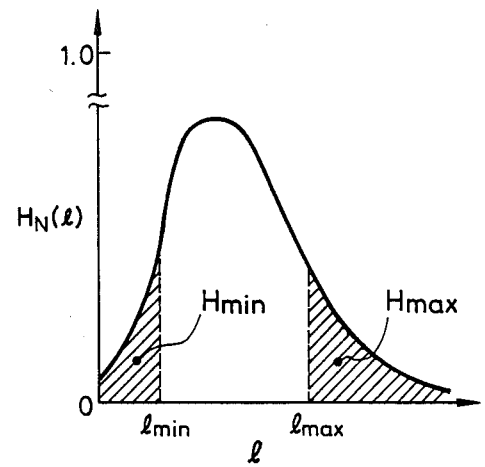

The normalized distribution thus obtained is shown in FIG. 9b. The normality or abnormality of the behavior of the fish can be judged by the comparison of the profile of this normalized distribution in the same manner as described in the foregoing, because, as shown in FIG. 10, there is the remarkable difference between the profile of the normalized distribution under the normal behavior of the fish and that of the normalized distributions under the abnormal behavior of the fish.

However, in this embodiment, there will be disclosed a somewhat different method for detecting the abnormality of the behavior of the fish. The total frequencies of the extremely slow movement of the fish and the total frequencies of the extremely fast movement thereof are obtained. This is based on the following. The extremely slow movement of the fish indicates that the fish is already damaged considerably by the toxicant contamination of water, and the extremely fast movement thereof indicates that the fish is furiously moving at the abnormally high speed because of the toxicant contamination of water.

Namely, in the normalized distribution of FIG. 9b, the area $H_{min}$ of the portion in the moving speed lower than a predetermined value $l_{min}$ and the area $H_{max}$ of the portion in the moving speed higher than another predetermined value $l_{max}$ (both hatched in the figure) are calculated at step 834. Next, at step 836, it is discriminated whether or not $H_{min}$ is smaller than a predetermined minimum limit $H_{min}$ or whether or not $H_{max}$ is larger than a predetermined maximum limit $HR_{max}$. If the answer of the discrimination in step 836 is negative, the operation ends and waits the start of the next time of the observation. However, if the answer in step 836 is positive, the alarm signal is given to the alarm device 48 at step 838 and thereafter the operation ends.

Figure 11A:
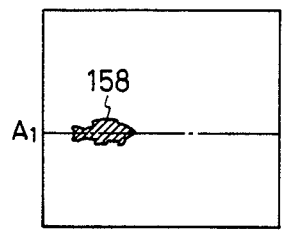
FIGS. 11a to 11c and FIGS. 12a to 12c are drawings for explaining another manner of operation of FIGS. 8a and 8b.
Figure 11B:
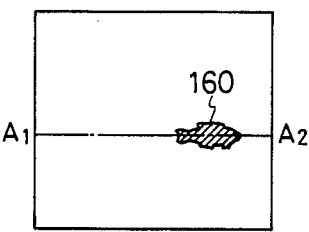
Figure 11C:
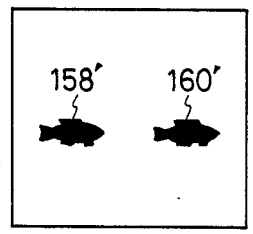
Figure 12A:
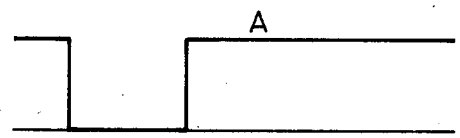
Figure 12B:
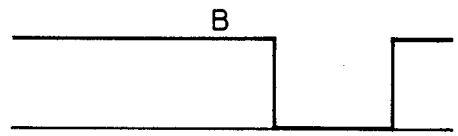

In the following, the explanation will be made of another method of obtaining the moving speed of the fish, referring to FIGS. 11 and 12. In this method, there is used the differential image between two gray images taken at different time points. For the simplicity of the explanation, let us assume that a fish moves just horizontally. Accordingly, a gray image as shown in FIG. 11a, which includes a fish image 158, is taken at the time point $t_0$, and after the time $\Delta t$ from the time point $t_0$, a gray image as shown in FIG. 11b, which includes a fish image 160, is obtained. If both the gray images are scanned along the line $A_1$-$A_2$, the brightness distributions A and B as shown in FIGS. 12a and 12b are obtained with respect to pixels on the line $A_1$-$A_2$.

Figure 12C:
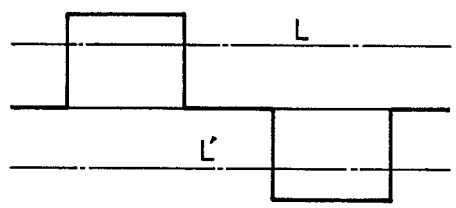

Then, if the subtraction is carried out between the brightness distributions A and B, a ternary signal as shown in FIG. 12c is obtained. Further, such a ternary signal is compared with two thresholds L and L'(=|L|), as shown in FIG. 12c. The scanning and the comparison as mentioned above is conducted over the whole of the image.

The comparison output is made "0", when the brightness level is higher than L or lower than L' and "1", when the brightness level lies between L and L'. If "0" is expressed by black and "1" by white, the binary image as shown in FIG. 11c, which includes both the fish images 158' and 160', is obtained on the basis of the ternary image data as shown in FIG. 12c.

After that, the gravity centers of the respective fish images are calculated. If the distance between the thus obtained gravity centers is measured and divided by the time $\Delta t$, the moving speed of the fish can be obtained.

By the way, the monitoring accuracy of the method mentioned above is much improved by further taking account of the acceleration of the movement of a fish. In the following, the explanation will be made of the processing operation of the improved method, referring to a flow chart of FIG. 13. In the figure, there are shown only processing steps to be added as well as the related steps in the flow chart of FIGS. 8a and 8b. Therefore, in the figure, the same reference numerals denote the same processing steps as in FIGS. 8a and 8b.

Figure 13:
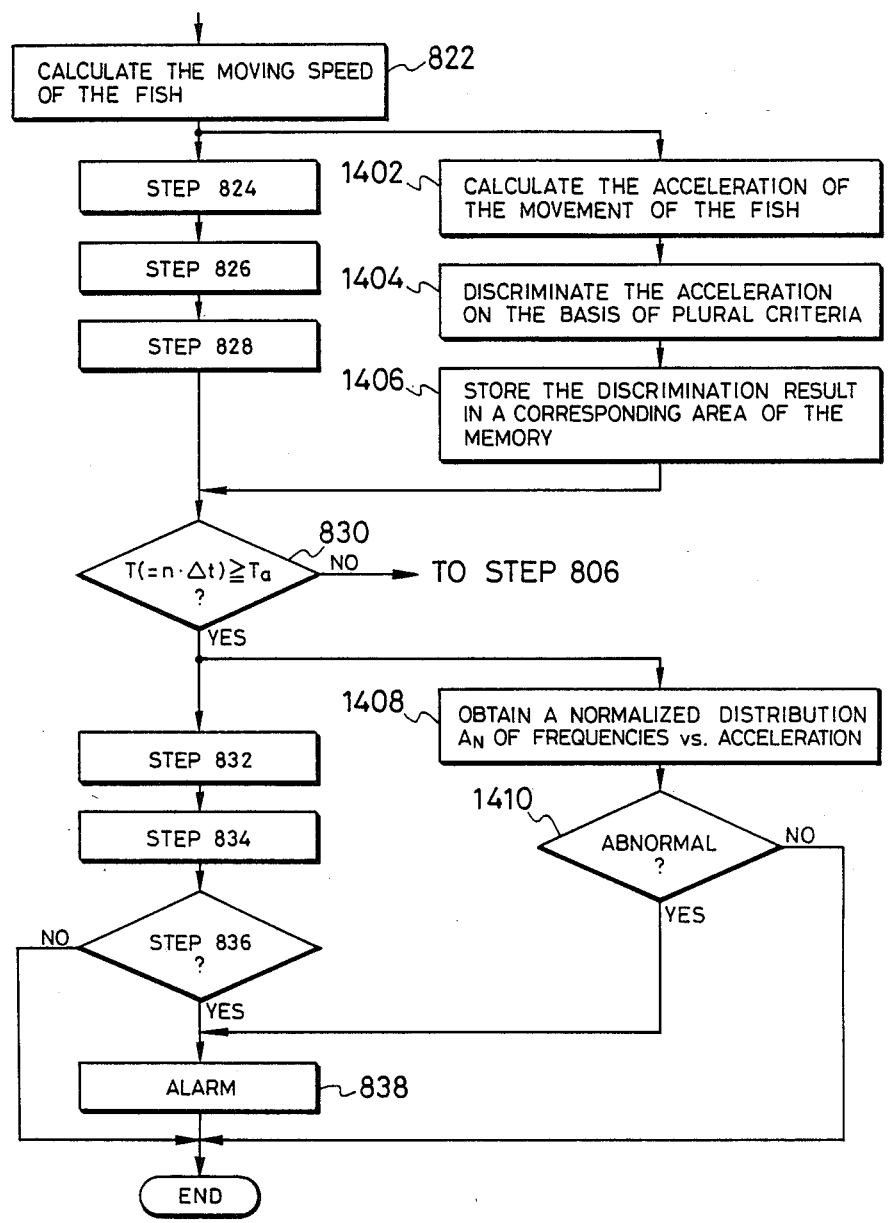
FIG. 13 is a flow chart showing the improvement of the operation illustrated by the flow chart of FIGS. 8a and 8b.

In FIG. 13, after the moving speed of a fish is calculated at step 822, the operation goes to step 1402 as well as to step 824. The explanation of the processing steps following step 824 is omitted, because the operation thereof has been already described.

At step 1402, the acceleration $A_n$ in the movement of the fish is calculated by further dividing the moving speed $V_n$ of the fish obtained in step 822 by $\Delta t$. Then, at step 1404, the obtained acceleration $A_n$ is compared with plural criteria A (p) (p=1, 2, ...., P) prepared for the discrimination of the acceleration, wherein p is an integer representing a class of the criteria. if $A(p) \leq A_n < A(p+1)$, the discrimination result is made p. On the other hand, there are provided in a memory of the system processor 42 plural storage areas each operating as a counter, the number of which is equal to that P of the criteria prepared for the aforesaid discrimination, and each of which corresponds to the respective discrimination result p. At step 1406, the discrimination result is stored. Namely, when the calculated acceleration $A_n$ meets the aforesaid relation, the content of the counter area corresponding to the discrimination result p is increased by one.

Thereafter, at step 830, it is discriminated whether or not the lapse of time T from the beginning of the observation exceeds $T_a$ set for one observation time period. If T does not exceeds $T_a$, the operation returns to step 806 (cf. FIG. 8a). Further, after step 822, the processing operation of steps 824 to 830 and that of steps 1402 to 830 are carried out alternately on the time-sharing basis.

Figure 14A:
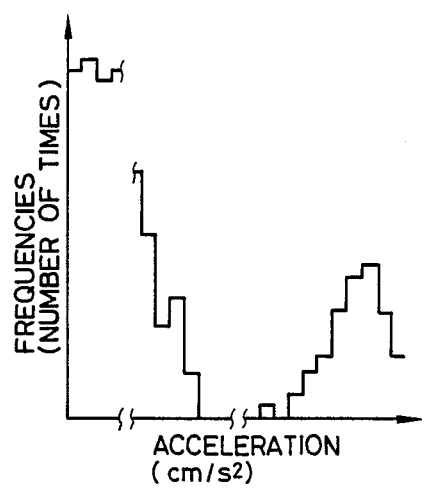
FIGS. 14a and 14b are drawings for explaining the operation illustrated by the flow chart of FIG. 13.

Similarly to the case of the moving speed, the number N of times of the loop operation are carried out and the number N of data of the acceleration are obtained. As the result of the repetition of the loop operation, the distribution of frequencies versus the accelerations is obtained as shown in FIG. 14a.

If it is judged at step 830 that T reaches $T_a$, the operation goes to step 1408 as well as to step 832. Similarly to step 832, a normalized distribution of frequencies versus the accelerations is obtained at step 1408 in accordance with the following formular:

$$A_N(p) = A(p)/N \tag{7}$$

wherein A(p) represents the frequencies of the acceleration belonging to the class p of the criteria and $A_N(p)$ a normalized value thereof.

Figure 14B:
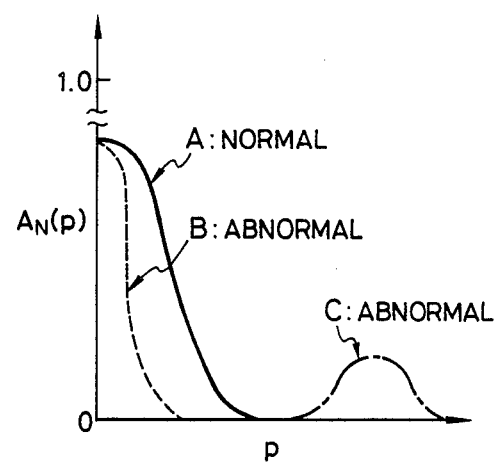

Examples of the thus obtained normalized distribution are shown in FIG. 14b. As apparent from the figure, there is the remarkable difference between the profile of the distribution under the normal behavior of the fish, as shown by a solid line A in the figure, and that under the abnormal behavior thereof as shown by a broken line B or a chain line C. During the fish shows the normal behavior, the extremely high acceleration as shown by the chain line C does not appear in the normalized distribution and the distribution of the acceleration is not biased extremely on the side of the low acceleration as shown by the broken line B.

Therefore, the normality or abnormality of the behavior of the fish can be judged by the comparison of the profile of the distribution. This comparison is carried out at step 1410. If the abnormality is not detected, the operation returns to step 802 (cf. Fig. 8a). Otherwise, the alarm signal is given to the alarm device 48 at step 838 and the operation ends.

As apparent from the flow of FIG. 13, especially from the portion of steps 836 and 1410, the alarm is given in this example, when the abnormality is detected in the moving speed of the fish and/or when it is detected in the acceleration thereof. As a variation of this method, however, it is possible to give the alarm signal only when the abnormality is detected in both the moving speed and the acceleration simultaneously. With this, the reliability of the alarm is raised, although the sensitivity of the monitoring may be somewhat reduced. The choice depends on the reliability and sensitivity required of the monitoring system. monitored simultaneously. It will be understood from the description above, however, that the abnormality of the behavior of the fish can be detected by the acceleration only. In this case, of course, steps 824, 826, 828, 832, 834 and 836 becomes unnecessary.

By the way, a fish continues to move its fins, especially pectoral fins, in order to keep its balance, even during it stays at a one place within water. Therefore, the condition of the fish can be monitored more strictly by observing the movement of the fins. Namely, it is prevented to erroneously regard the standstill of the fish as the toxicant contamination of water. Such an erroneous judgment may occur, if the behavior of the fish is monitored by observing only the gravity center of a fish image, the moving speed of the fish, or the acceleration in the movement thereof.

Figure 15A:
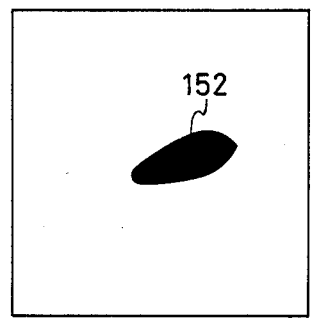
FIGS. 15a and 15b, FIGS. 16a and 16b and FIG. 17 are drawings showing an example of the method for further improving the accuracy in the observation of the behavior of an aquatic animal.
Figure 15B:
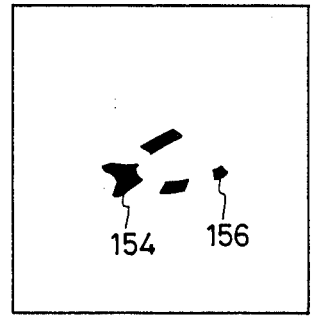

In order to observe the movement of the fins of a fish, the image of the fins must be recognized separately from the body of the fish. To this end, it is utilized that there is the difference in the brightness between the body of the fish and the fins thereof, as already described. There is prepared another threshold $L_2$ as shown in FIG. 6b. With this threshold $L_2$, only a binary image of the body of the fish is extracted, and thereafter if the subtraction is carried out between the binary image as shown in FIG. 6d and that of the body of the fish mentioned above, a binary image of the fins only can be obtained. The binary image of the body 152 and that of the fins 154, 156 are shown in FIGS. 15a and 15b, respectively.

Now, the movement of the fins is monitored on the thus obtained binary image of the fins as follows. The following explanation will be made, taking the monitoring of a pectoral fin as an example.

Figure 16A:
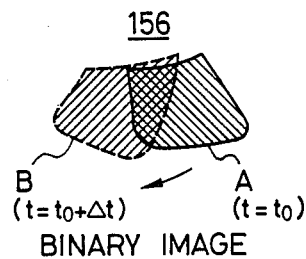
Figure 16B:
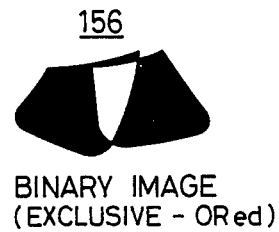

FIG. 16a shows a binary image illustrating an example of the movement of the pectoral fin. It is to be noted, however, that the two images A and B taken at the different time points $t_0$ and $t_0 + \Delta t$ are included in the figure overlapping each other. If these two images A and B are exclusive-ORed, the binary image as shown in FIG. 16b is obtained. As apparent from FIG. 16b, there lacks the portion overlapping in FIG. 16a. Therefore, the area of the image in FIG. 16b represents the amount of movement of the pectoral fin.

Figure 17:
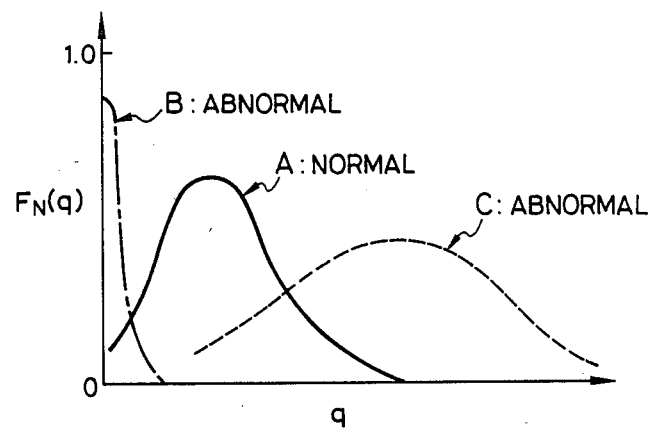

Similarly to the cases already mentioned, the distribution of frequencies versus the amount of movement of the fin is obtained and normalized. Examples of the normalized distribution are shown in FIG. 17. During the fish is normal, the normalized distribution becomes as shown by a solid line A in the figure. If the fish is abnormal because of the toxicant contamination, the movement of the fin is extremely reduced as shown by a chain line B or the fin is moved radically as shown by broken line C. It may be judged on only the normalized distribution of the moving speed of the fish, for example, that the behavior of the fish is abnormal because of the very slow movement of the fish. Even in such a case, the erroneous judgment can be avoided by monitoring the movement of the fin, as mentioned above.

Figure 18:
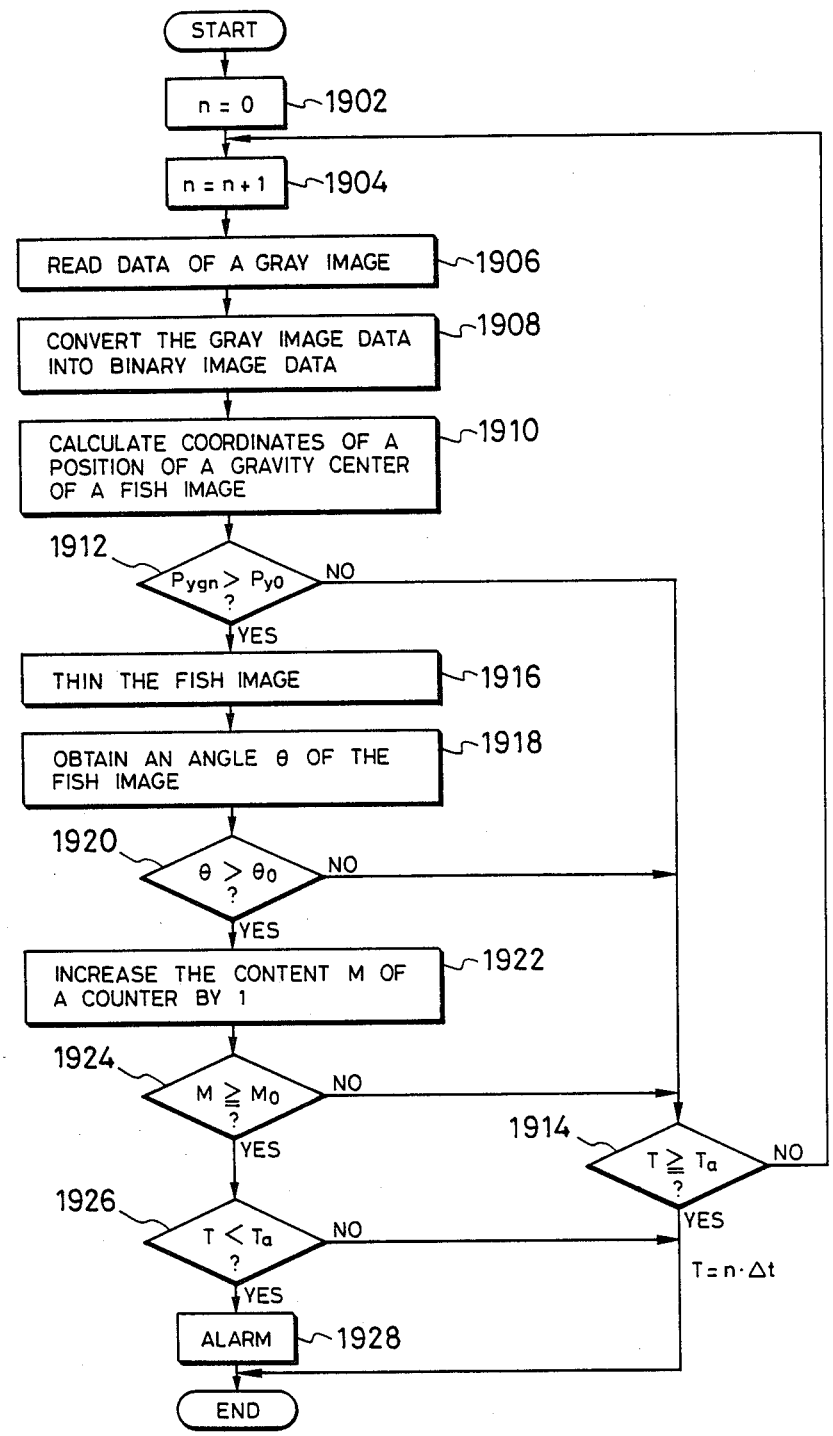
FIG. 18 is a flow chart of still another example of the operation of the data processing system of FIG. 4.

The abnormal behavior of a fish is also detected by the posture taken by a fish. The following embodiment concerns the monitoring of the posture of a fish. FIG. 18 shows a flow chart of the processing operation in this embodiment. Since steps 1902 to 1910 in this flow chart are quite the same as steps 502 to 510 in FIG. 5, the description thereof is omitted here.

After the gravity center of a fish image is calculated at step 1910, the vertical component $Y_{gn}$ is compared with a predetermined value $P_{y0}$ at step 1912. Since the value $P_{y0}$ is set at a value in the neighborhood of the surface of water, the fact that $y_{gn}$ exceeds $P_{y0}$ means that the fish is in the neighborhood of the surface of water. Further, if the fish takes the posture of the large angle with respect to the surface of water in the neighborhood thereof, it means that the fish takes the behavior of raising and moving its mouth over the surface of water. Such behavior is also a kind of abnormal behaviors. Therefore, it will be understood that the abnormality of the fish can be also detected by monitoring the angle of the fish made with respect to the surface of water If it is discriminated at step 1912 that $y_{gn}$ is smaller than $P_{y0}$, the operation goes to step 1914. Further, if it is discriminated at step 1914 that the lapse of time T exceeds $T_a$, the operation ends and waits the start of the next time of the observation. Otherwise, the operation returns to step 1904 and the same operation as mentioned above is repeated. The repetition of this operation is continued until T reaches $T_a$.

If it is judged at step 1912 that $y_{gn}$ is larger than $P_{y0}$, the operation goes to step 1916, at which the fish image is thinned in order to facilitate the detection of the angle of the fish with respect to the surface of water. The manner of thinning is shown in FIGS. 19a and 19b, in which the former drawing illustrates the binary image before the thinning and the later an image after the thinning. This thinning is well known in the field of the image processing technique.

Then, an angle $\theta$ of the fish image with respect to the surface of water is obtained at step 1918. The calculation of the angle $\theta$ is carried out as follows. In FIG. 20, which shows the thinned image of the fish, coordinates $(x_1, y_1)$ and $(x_2, y_2)$ of both ends $P_1$ and $P_2$ of the thinned image are at first obtained and then the angle $\theta$ is calculated in accordance with the following formula:

$$\tan \theta = \frac{|y_1 - y_2|}{|x_1 - x_2|} \tag{8}$$

The thus obtained angle $\theta$ is compared with a predetermined value $\theta_0$ at step 1920. If $\theta$ is smaller than $\theta_0$, the operation goes to step 1914 and, if T exceeds $T_a$, it ends and waits the start of next time of the observation. Otherwise, the operation returns to step 1904, and the same operation is repeated. The repetition of this operation continues until T reaches $T_a$.

If it is discriminated at step 1920 that $\theta$ is larger than $\theta_0$, the operation goes to step 1922, at which the content M of a counter provided for counting the discrimination result in the memory of the system processor 42 is increased by one. Thereafter, the content M of the counter is compared with a predetermined value $M_0$ at step 1924. If M is smaller than $M_0$, the operation goes to step 1914. Further, if T does not exceed $T_a$, the operation ends and waits the start of next time of the observation. Otherwise, the operation returns to step 1904, and the same operation is repeated, after n is increased by one. This repetition of the operation continues until T reaches $T_a$.

If it is judged at step 1924 that M exceeds $M_0$, the operation goes to step 1926, and, if T exceeds $T_a$, it ends. If, however, T does not exceed $T_a$, the operation goes to step 1928, at which the alarm signal is given to the alarm device 48. Thereafter, the operation ends and waits the start of the next time of the observation.

The operation in steps 1914, 1924 and 1926 is explained in detail, referring to FIG. 21. As shown in the figure, the number of times that the fish takes the postural angle larger than the predetermined value in the neighborhood of the surface of water are counted up by the counter, and the alarm signal is given, when the content M of the counter exceeds the predetermined value $M_0$ within the observation time $T_a$, as shown by a broken line B in FIG. 21. During the fish is normal, the content M of the counter never exceeds $M_0$ within $T_a$, as shown by a solid line A in the figure.

In the foregoing, there have been described several kinds of methods of processing the image of an aquatic animal, which is bred for monitoring the toxicant contamination of water. Although each of those methods can be utilized individually, it is also possible to combine some of them, which are selected in accordance with circumstances, such as the accuracy, sensitivity or reliability required of the monitoring.

As described above, according to the present invention, an aquatic animal, which is bred for monitoring the toxicant contamination of water, is accurately observed by the image processing technique without the influence of seasonal change in the color of the body of the aquatic animal or other factors. Further, the monitoring is performed at the high accuracy by processing the image taken in the good condition mentioned above in accordance with the improved method disclosed herein.

We claim:

1. A method for determining the presence of toxicant contamination of water using a monitoring apparatus having a basin into which water to be tested is introduced and in which an aquatic animal is bred and a television camera for taking an image of a predetermined area of the basin, said monitoring apparatus including
   a memory unit operating as a binary image memory for storing data of a binary image obtained by converting a gray image data taken by the television camera and a processing unit programed so as to execute various operations, comprising the steps of:
   (a) calculating a position of a gravity center of an image of the aquatic animal from the binary image data stored in said memory unit;
   (b) discriminating a component of the calculated gravity center in a vertical direction of the water on the basis of plural criteria prepared in advance;
   (c) repeating steps (a) and (b) for an observation time period to obtain a distribution frequency of calculated gravity centers with respect to the plural criteria; and
   detecting an abnormal behavior of the aquatic animal on the basis of the distribution frequency of the calculated gravity centers obtained at step (c), said detected abnormal behavior indicating the presence of toxicant contamination of the water.

2. An apparatus for monitoring the toxicant contamination of water, comprising:
 a basin into which a part of water to be tested is introduced and in which an aquatic animal is bred;
 a light source, arranged on the side of one of the side walls of said basin, for lighting up said basin;
 a television camera, arranged on the side of the other side wall of said basin opposite to the one side wall, for taking an image of a predetermined area of said basin, said image including an image of the aquatic animal; and,
 a processor for processing plural images taken by said television camera during a predetermined observation time period to obtain a frequency distribution of gravity centers of images of the aquatic animal in a vertical direction of the water, and producing an alarm signal, when the behavior of the aquatic animal is judged as being abnormal on the basis of the obtained frequency distribution of gravity centers.

3. An apparatus as defined in claim 2, wherein there is further provided a translucent plate between said basin and said light source.

4. An apparatus as defined in claim 2, wherein various environmental factors of said water to be tested are adjusted before said water is introduced into said basin.

5. An apparatus as defined in claim 2, wherein the alarm signal is produced, when there occurs a peak of the frequency distribution in the neighborhood of the surface of the water or when the frequency distribution is substantially flat in the vertical direction of the water.

6. An apparatus as defined in claim 2, wherein said processor further obtains a frequency distribution of moving speed of the aquatic animal by processing the plural images taken by said television camera, and produces the alarm signal, when the behavior of the aquatic animal is judged as being abnormal on the basis of the frequency distribution of gravity centers and the frequency distribution of moving speed.

7. An apparatus for monitoring the toxicant contamination of water, comprising:
 a basin which a part of water to be tested is introduced and in which an aquatic animal is bred;
 a light source, provided on one side of said basin, for lighting up said basin;
 a television camera, provided on the other side of said basin opposite to the one side, for taking an image of a predetermined area of said basin, said image including an image of the aquatic animal; and
 a processor for processing plural images taken by said television camera during a predetermined observation time period to obtain a frequency distribution of moving speed of the aquatic animal, and producing an alarm signal, when a total frequency of the movement of the aquatic animal which is slower than an first predetermined speed exceeds a first predetermined frequency or when a total frequency of the movement of the aquatic animal which is faster than a second predetermined speed exceeds a second predetermined frequency.

8. An apparatus as defined in claim 7, wherein the moving speed of the aquatic animal is obtained by a subtraction of positions between two images taken by said camera at different time points.

9. An apparatus as defined in claim 7, wherein the abnormal behavior of the aquatic animal is judged on the basis of a comparison of a profile of the frequency distribution of the moving speed obtained during one observation time period with a profile of a reference frequency distribution of the moving speed prepared in advance.

10. An apparatus for monitoring the toxicant contamination of water, comprising:
 a basin into which a part of water to be tested is introduced and in which an aquatic animal is bread;
 a light source, provided on one side of said basin, for lighting up said basin;
 a television camera, provided on the other side of said basin opposite to the one side, for taking an image of a predetermined area of said basin, said image including an image of the aquatic animal; and,
 a processor for processing plural images taken by said television camera during a predetermined observation time period to obtain a frequency distribution of acceleration in the movement of the aquatic animal, and producing an alarm signal, when the behavior of the aquatic animal is judged as being abnormal on the basis of the obtained frequency distribution of acceleration.

11. An apparatus for monitoring the toxicant contamination of water, comprising:
 a basin into which a part of water to be tested is introduced and in which an aquatic animal is bred;
 a light source, provided on one side of said basin, for lighting up said basin;
 a television camera, provided on the other side of said basin opposite to the one side, for taking an image of a predetermined area of said basin, said image including an image of the aquatic animal; and
 a processor for processing plural images of the aquatic animal taken by said television camera during a predetermined observation time period to obtain a frequency distribution of moving speed of the aquatic animal and a frequency distribution of acceleration in the movement of the aquatic animal, and producing an alarm signal, when the behavior of the aquatic animal is judged as being abnormal on the basis of the obtained frequency distributions of moving speed and acceleration.

12. An apparatus for monitoring the toxicant contamination of water, comprising:
 a basin into which a part of water to be tested is introduced and in which a fish is bred;
 a light source, provided on one side of saidbasin, for lighting up said basin,
 a television camera, provided on the other side of said basin opposite to the one side, for taking an image of a predetermined area of said basin, said image including an image of the fish; and
 a processor for processing plural images taken by said television camera during a predetermined observation time period to obtain a frequency distribution of the amount of movement of fins of the fish, and producing an alarm signal, when the behavior of the fish, and producing an alarm signal, when the behavior of the fish is judged as being abnormal on the basis of the obtained frequency distribution of the amount of movement of the fins.

13. An apparatus for monitoring the toxicant contamination of water, comprising:
 a basin into which a part of water to be tested is introduced and in which a fish is bred;
 a light source, provided on one side of said basin, for lighting up said basin;

a television camera, provided on the other side of said basin opposite to the one side, for taking an image of a predetermined area of said basin, said image including an image of the fish; and, a processor for processing plural images taken by said television camera during a predetermined observation time period to count the number of times than an angle of the fish with respect to the surface of the water is larger than a predetermined value, and producing an alarm signal when a counted value exceeds a predetermined value within the observation time period.

* * * * *